(12) United States Patent
Shiratani (10) Patent No.: US 10,860,930 B2
(45) Date of Patent: Dec. 8, 2020

(54) LEARNING METHOD, IMAGE RECOGNITION DEVICE, AND COMPUTER-READABLE STORAGE MEDIUM

(71) Applicant: OLYMPUS CORPORATION, Hachioji (JP)

(72) Inventor: Fumiyuki Shiratani, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 118 days.

(21) Appl. No.: 16/150,933

(22) Filed: Oct. 3, 2018

(65) Prior Publication Data
US 2019/0034800 A1 Jan. 31, 2019

Related U.S. Application Data

(63) Continuation of application No. PCT/JP2016/061045, filed on Apr. 4, 2016.

(51) Int. Cl.
*G06N 3/08* (2006.01)
*G06N 20/10* (2019.01)
(Continued)

(52) U.S. Cl.
CPC ............ *G06N 3/084* (2013.01); *A61B 1/00* (2013.01); *A61B 1/00009* (2013.01); *G06K 9/4628* (2013.01); *G06K 9/6269* (2013.01); *G06K 9/6274* (2013.01); *G06N 3/0427* (2013.01); *G06N 3/0454* (2013.01); *G06N 20/10* (2019.01); *G06T 7/0012* (2013.01); *G06T 7/70* (2017.01); *A61B 1/041* (2013.01); *G06K 2209/051* (2013.01); *G06T 2207/10068* (2013.01);
(Continued)

(58) Field of Classification Search
None
See application file for complete search history.

(56) References Cited

U.S. PATENT DOCUMENTS 10,482,313 B2 * 11/2019 Murthy ................ G06T 7/0012
2007/0122036 A1 5/2007 Kaneda et al.
(Continued)

FOREIGN PATENT DOCUMENTS

JP 2007087345 A 4/2007
JP 2015036123 A 2/2015

OTHER PUBLICATIONS

International Search Report (ISR) dated Jun. 21, 2016 issued in International Application No. PCT/JP2016/061045.
(Continued)

*Primary Examiner* — Vikkram Bali
(74) *Attorney, Agent, or Firm* — Holtz, Holtz & Volek PC (57) ABSTRACT

A learning method performed by an image recognition device is provided which includes a convolutional neural network. The learning method includes performing first learning by the convolutional neural network by using a first image group captured at a first frame rate, the first image group being input from outside; and performing, after performing the first learning, second learning by using a second image group that is captured at a second frame rate that is lower than the first frame rate, the second image group being is input from outside, and the number of images in the second image group being less than that in the first image group.

16 Claims, 9 Drawing Sheets

(51) Int. Cl.
*G06K 9/46* (2006.01)
*A61B 1/00* (2006.01)
*G06N 3/04* (2006.01)
*G06K 9/62* (2006.01)
*G06T 7/70* (2017.01)
*G06T 7/00* (2017.01)
*A61B 1/04* (2006.01)

(52) U.S. Cl.
CPC ............. *G06T 2207/20081* (2013.01); *G06T 2207/20084* (2013.01); *G06T 2207/30028* (2013.01); *G06T 2207/30092* (2013.01)

(56) References Cited

U.S. PATENT DOCUMENTS

| | | |
|---|---|---|
| 2013/0322770 A1 | 12/2013 | Kaneda et al. |
| 2015/0043772 A1 | 2/2015 | Poole et al. |
| 2017/0200063 A1* | 7/2017 | Nariyambut Murali ..................... G06T 1/20 |
| 2018/0075599 A1* | 3/2018 | Tajbakhsh ............. G06T 7/0012 |

OTHER PUBLICATIONS

Written Opinion dated Jun. 21, 2016 issued in International Application No. PCT/JP2016/061045.
Nima Tajbakhsh et al., "Convolutional Neural Networks for Medical Image Analysis: Full Training or Fine Tuning?," IEEE Transactions on Medical Imaging, May 2016, vol. 35, No. 5, pp. 1299-1312.

* cited by examiner

LEARNING METHOD, IMAGE RECOGNITION DEVICE, AND COMPUTER-READABLE STORAGE MEDIUM

CROSS-REFERENCE TO RELATED APPLICATION

This application is a continuation of International Application No. PCT/JP2016/061045, filed on Apr. 4, 2016, the entire contents of which are incorporated herein by reference.

BACKGROUND OF THE INVENTION

1. Field of the Invention

The present disclosure relates to a learning method and an image recognition device which utilize a convolutional neural network that learns from some image groups and recognizes for other image groups, and a non-transitory computer-readable storage medium storing executable instructions for the learning method and the image recognition device to operate.

2. Description of the Related Art

In a field of medical diagnosis, computer-aided diagnosis technologies have been known which enable, for example, an automatic classification of organs and a detection of lesions from images captured of a subject under diagnosis. Among such technologies, there is a technology that is capable of automatically specifying the most probable position of a landmark as a reference point, in order to align or superimpose correlated images of the subject captured by a computed tomography (CT) scanner (see Japanese Laid-open Patent Publication No. 2015-36123). This technology allows a classifier to perform learning (training) by using a first medical image whose landmark position is already known, and then causes the classifier to specify the landmark position associated with a second medical image whose landmark position is unknown.

SUMMARY OF THE INVENTION

The present disclosure has been made in view of the above, and is directed to an improvement in computer-aided diagnosis technologies.

According to a first aspect of the present disclosure, a learning method performed by an image recognition device is provided which includes a convolutional neural network. The learning method includes performing first learning by the convolutional neural network by using a first image group captured at a first frame rate, the first image group being input from outside; and performing, after performing the first learning, second learning by using a second image group that is captured at a second frame rate that is lower than the first frame rate, the second image group being input from outside, and the number of images in the second image group being less than that in the first image group.

According to a second aspect of the present disclosure, an image recognition device that includes a convolutional neural network is provided. The image recognition device includes a processor comprising a hardware, the processor being configured to: acquire a first image group captured at a first frame rate and a second image group captured at a second frame rate that is lower than the first frame rate, the number of images in the second image group being less than that in the first image group; calculate, after the first image group is input to the convolutional neural network, a first error between an output result of the convolutional neural network and a correct answer label attached to the first image group; and update the weights in the convolutional neural network by back propagation performed on the first error through the convolutional neural network.

According to a third aspect of the present disclosure, an image recognition apparatus is provided which includes a processor that performs processing based on a convolutional neural network. The convolutional neural network has been learned by performing first learning by the convolutional neural network, by using a first image group captured at a first frame rate that is input from outside; and second learning, after performing the first learning, by using a second image group that is captured at a second frame rate lower than the first frame rate that is input from outside, the number of images in the second image group being less than that in the first image group.

The above and other features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

In the following, a learning method, an image recognition device, and a non-transitory computer-readable storage medium storing executable instructions, according to embodiments of the present disclosure, will be described. The present disclosure is not limited to the following embodiments. Additionally, in the drawings, components that are identical to those in embodiments are assigned the same reference numerals.

First Embodiment

Configuration of a Learning System

Figure 1:
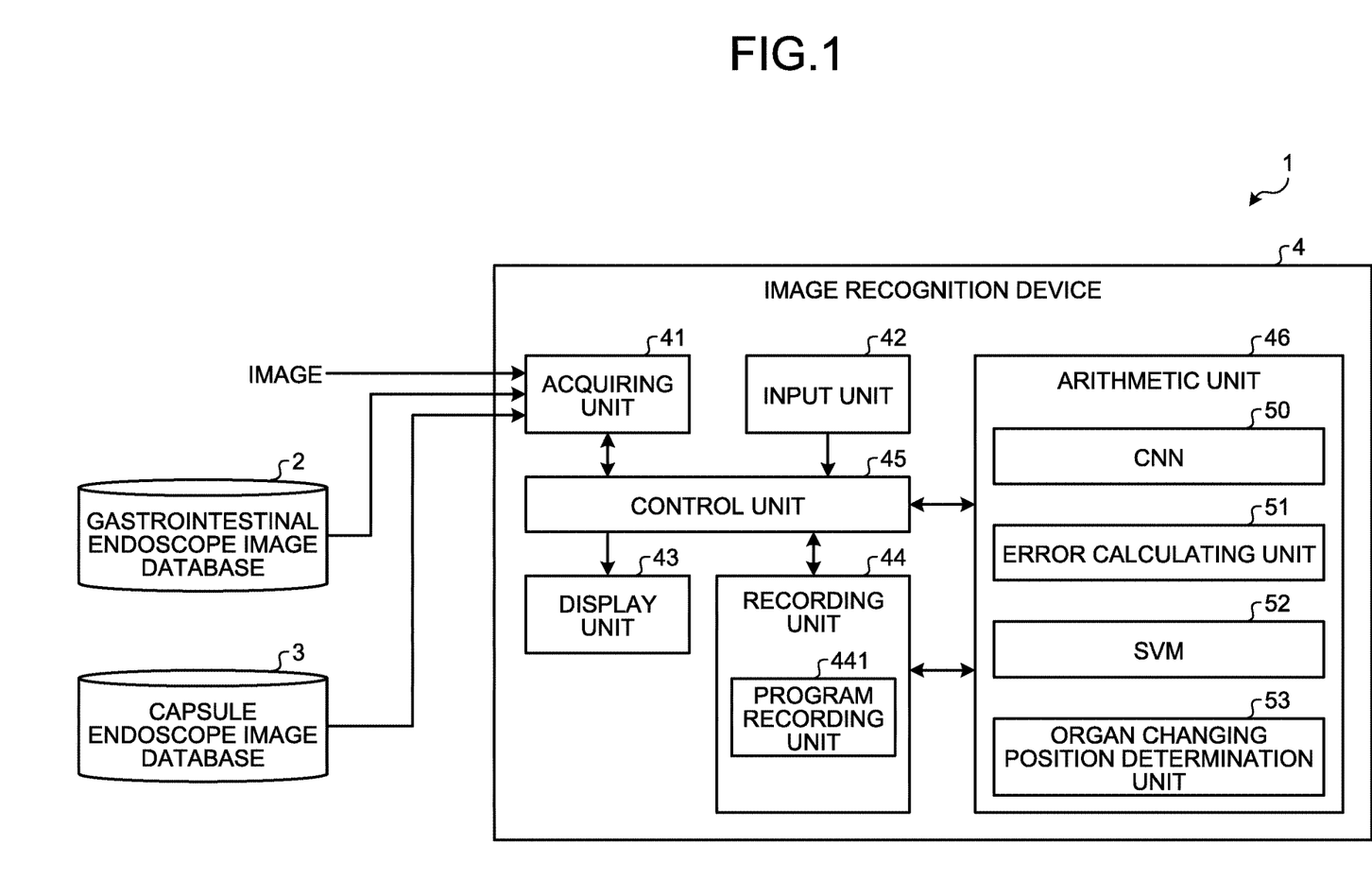
FIG. 1 is a block diagram illustrating the configuration of a learning system according to a first embodiment of the present disclosure.

FIG. 1 is a block diagram illustrating the configuration of a learning system according to a first embodiment of the present disclosure. A learning system 1 according to the first embodiment is a system that performs, as an example, a learning process of performing learning based on intraluminal images acquired by capturing an image of a lumen of the subject, a recognition process of performing recognition, and a landmark process of classifying positions of landmarks each representing the section of organs, such as the pylorus of the stomach or the ileocecal valve of the large intestine, or classifying the sections of organs. The intraluminal images may be acquired from a lumen of the subject by using an endoscope, which may include a gastrointestinal endoscope, such as a flexible endoscope or a rigid endoscope, which is inserted into the subject thereby to capture an inside of the subject, and a capsule endoscope that is swallowed by a subject and is discharged outside after a predetermined period of time.

The learning system 1 illustrated in FIG. 1 includes a gastrointestinal endoscope image database 2, a capsule endoscope image database 3, and an image recognition device 4. The gastrointestinal endoscope image database 2 stores image data groups of images obtained by capturing an inside of a subject by using a gastrointestinal endoscope, and correct answer labels that are used to recognize the landmarks. The capsule endoscope image database 3 stores image data groups of images obtained by capturing an inside of a subject by using a capsule endoscope, and correct answer labels that are used to recognize the landmarks. The image recognition device 4, which includes a convolutional neural network, acquires image data of intraluminal images from one of the gastrointestinal endoscope image database 2, the capsule endoscope image database 3, and an external unit, and learns and recognizes the images. Additionally, the gastrointestinal endoscope image database 2, the capsule endoscope image database 3, and the image recognition device 4 may also be connected so as to be capable of performing bidirectional communications via a network. In this case, these units may also be connected wirelessly or with a cable.

Gastrointestinal Endoscope Image Database

The gastrointestinal endoscope image database 2 is configured of a recording medium, such as a hard disk. The gastrointestinal endoscope image database 2 stores image data groups of images captured at a first frame rate by a gastrointestinal endoscope that can be inserted into a subject (hereinafter, referred to as a "first image group") and stores the correct answer labels for recognizing the landmark (hereinafter, referred to as a "first correct answer label"). Here, the first frame rate is, for example but not limited to, 60 fps or 30 fps. Additionally, the first correct answer label is an identifier (for example: +1 or −1) that allows the image recognition device 4 to learn the landmarks. The first correct answer label is attached to each of the images that have been selected in advance from the first image group, depending on whether or not a landmark is in the image.

Capsule Endoscope Image Database

The capsule endoscope image database 3 is configured of a recording medium, such as a hard disk. The capsule endoscope image database 3 stores second image group that is an image data group of images captured at the second frame rate by a capsule endoscope (hereinafter, referred to as a "second image group") and stores correct answer labels for recognizing the landmark (hereinafter, referred to as a "second correct answer label"). Incidentally, the number of images in the second image group is smaller than the number of images in the first image group. For example but not limited to, the second image group includes 50,000 images, while the first image group includes 500,000 images. Here, the second frame rate is, for example but not limited to, 2 fps. Additionally, the second image group is an image group obtained from interval shooting. Furthermore, the second correct answer label is an identifier (for example: +1 or −1) that allows the image recognition device 4 to learn the landmarks. The second correct answer label is attached to each of the images that have been selected in advance from the second image group, depending on whether or not a landmark is in the image.

Detailed Configuration of the Image Recognition Device

The image recognition device 4 includes an acquiring unit 41, an input unit 42, a display unit 43, a recording unit 44, a control unit 45, and an arithmetic unit 46. The acquiring unit 41 acquires image groups from one of the gastrointestinal endoscope image database 2, the capsule endoscope image database 3, and an external unit. The input unit 42 receives an input signal that is input by an operation from outside. The display unit 43 displays images and various kinds of information. The recording unit 44 records various programs and the image groups acquired by the acquiring unit 41. The control unit 45 performs overall control of the image recognition device 4. The arithmetic unit 46 learns from some image groups and recognizes for other image groups. If a portable recording medium is used to receive and send the image group, the acquiring unit 41 is configured of a reader device which the portable recording medium can be inserted to and removed from, and which reads the recorded image groups from the portable recording medium. Furthermore, if a server or a database that stores the image groups is used, the acquiring unit 41 is configured of a communication device or the like that can communicate with the server or the database via a network and then acquires the image group by performing data communication with the server or the database. Furthermore, the acquiring unit 41 may also be configured of an interface device or the like to which the image group is input from a gastrointestinal endoscope via a cable.

The input unit 42 is implemented by, for example, an input device, such as a keyboard, a computer mouse, a touch panel, and various switches. The input unit 42 inputs an input signal in accordance with an operation from outside and outputs the signal to the control unit 45.

The display unit 43 includes a display panel, such as a liquid crystal or an organic electro luminescence (EL) display panel. The display unit 43 displays various frames including images under the control of the control unit 45.

The recording unit 44 is configured of various memories, such as a flash memory, a read only memory (ROM), and a random access memory (RAM), or a hard disk that is connected by a data communication terminal. In addition to the image data acquired by the acquiring unit 41, the recording unit 44 records programs that operate the image recognition device 4 and that cause the image recognition device 4 to execute various functions. Moreover, the recording unit 44 records data or the like that is used during the program being executed. For example, the recording unit 44 includes a program recording unit 441 that records therein a program for learning from image groups that are input from the acquiring unit 41.

The control unit 45 is implemented by a central processing unit (CPU), or the like. By reading various programs recorded in the recording unit 44, in accordance with the image group that is input from the acquiring unit 41 or the input signal or the like that is input from the input unit 42, the control unit 45 gives an instruction or a transfer to each of the units that form the image recognition device 4 and performs overall control of the operation of the image recognition device 4. Furthermore, the control unit 45 performs back propagation of a first error calculated by an error calculating unit 51, which will be described later, in a convolutional neural network 50 (hereinafter, referred to as a "CNN 50"), thereby to update the weights of the parameters in the CNN 50. Furthermore, the control unit 45 updates the weights of the parameters in the CNN 50 by performing back propagation of a second error calculated by the error calculating unit 51, which will be described later, in the CNN 50.

The arithmetic unit 46 is implemented by a CPU or the like. The arithmetic unit 46 performs the learning process, the recognition process, and the landmark process on an image group by reading the program recorded by the program recording unit 441.

Detailed Configuration of the Arithmetic Unit

Figure 2:
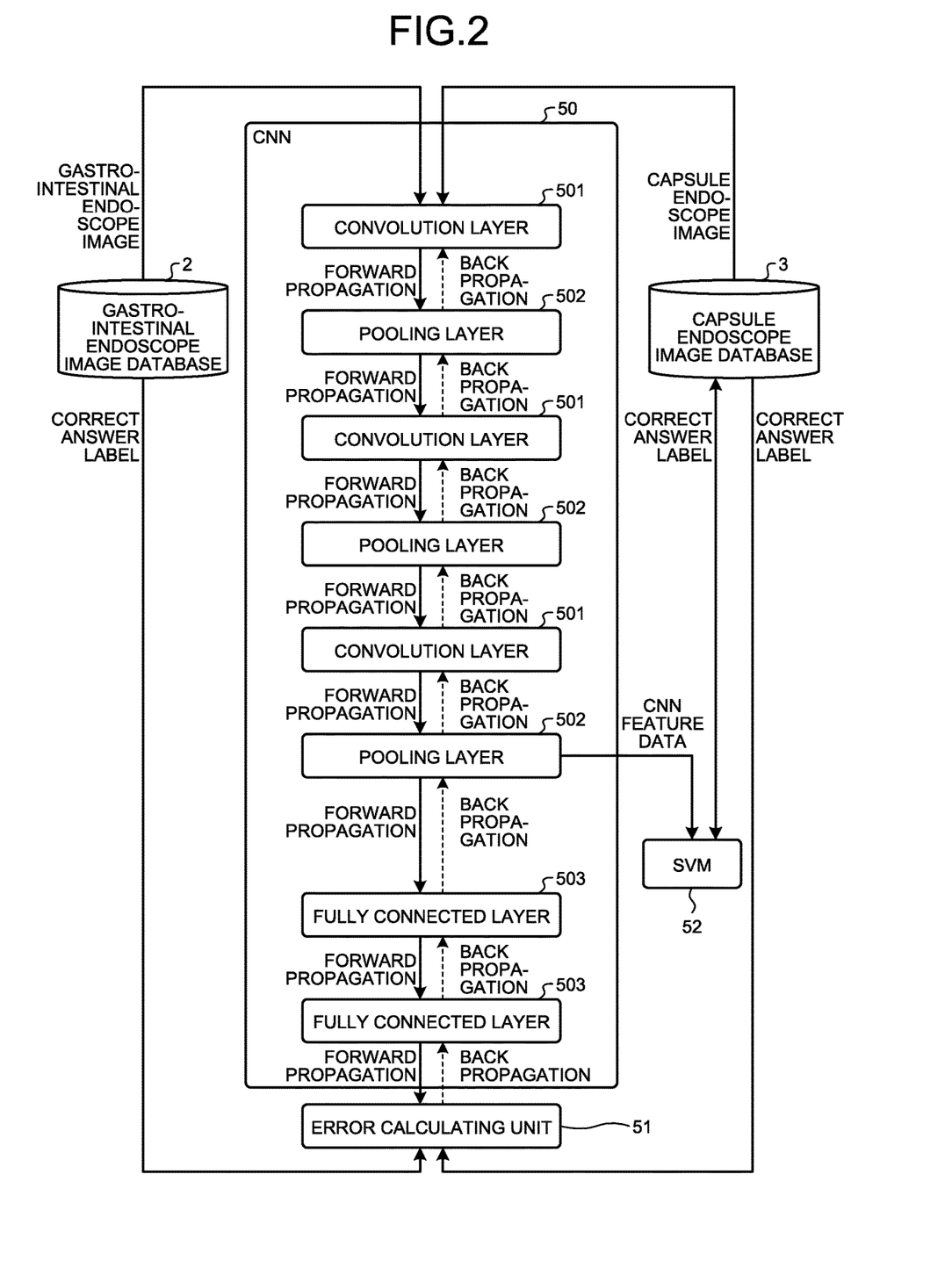
FIG. 2 is a schematic diagram illustrating, in outline, the configuration of an arithmetic unit in an image recognition device according to the first embodiment of the present disclosure.

In the following, the configuration of the arithmetic unit 46 will be described in detail with reference to FIG. 2 in addition to FIG. 1. FIG. 2 is a schematic diagram illustrating, in outline, the configuration of the arithmetic unit 46. As illustrated in FIG. 1, the arithmetic unit 46 includes the CNN 50, the error calculating unit 51, a support vector machine 52 (hereinafter, referred to as the "SVM 52"), and an organ changing position determination unit 53.

The CNN 50 performs learning by using the first image group acquired by the acquiring unit 41 from the gastrointestinal endoscope image database 2 and then performs learning by using the second image group acquired by the acquiring unit 41 from the capsule endoscope image database 3. Specifically, the CNN 50 performs a pre-training as a first learning, based on an error back propagation, using the first image group and the first correct answer labels, in order to decrease an error between the first image group and the first correct answer labels, thereby to update the weights of the parameters. Then, the CNN 50 performs a fine-tuning as a second learning, based on the error back propagation, using the second image group and the second correct answer labels, in order to decrease an error between the second image group and the second correct answer labels, thereby to update the weights of the parameters.

Referring to FIG. 2, the CNN 50 includes convolution layers 501, pooling layers 502 (sub sampling layers), and fully connected layers 503. While the CNN 50 is formed of the convolution layers 501 and the pooling layers 502 that are alternately repeated three times in the first embodiment, the CNN 50 may also be formed of the convolution layers 501 and the pooling layers 502 repeated at least one or more times or may also be formed of, for example, the convolution layers 501 and the pooling layers 502 that are repeated four times in other embodiments. Furthermore, while the CNN 50 is formed of the fully connected layers 503 that are repeated twice in the first embodiment, the fully connected layers 503 may be repeated one time or more, or the fully connected layers 503 are repeated, for example, three times, in other embodiments.

After the first image group is input to the CNN 50, the error calculating unit 51 calculates the first error between the output result of the CNN 50 and the first correct answer label. Furthermore, after the weights in the CNN 50 have been updated, when the second image group is input to the CNN 50, the error calculating unit 51 calculates the second error between the output result of the CNN 50 and the second correct answer label that is attached to the second image group.

After the weights of the parameters in the CNN 50 have been updated, by using an intermediate output of the CNN 50 extracted as (CNN) feature data of the second image group by the CNN 50 and by using the correct answer label of the second image group, the SVM 52 learns for classification of an input image or detection of a recognition target object. Furthermore, after having learned the second image group, the SVM 52 classifies input images by using the second image group or detects a recognition target object. Here, the input image is an organ image obtained by capturing, for example, an inner wall of a lumen organ, such as the stomach or the large intestine. The recognition target object is a lesion, such as a polyp, that is present on the surface of an inner wall of, for example, a lumen organ. Furthermore, in the first embodiment, the SVM 52 functions as a learning machine; however, the configuration is not limited to this and another learning machine may also be combined.

Based on a degree of similarity between the determination result in which the sections of organs has been determined (classified) by the SVM 52 and a step function, which will be described later, the organ changing position determination unit 53 extracts (determines) a candidate for a changing position of organs, for example, a changing position between the stomach and the small intestine and determines a correct answer changing position of organs, such as the pylorus or the ileocecal valve.

Learning Process

Figure 3:
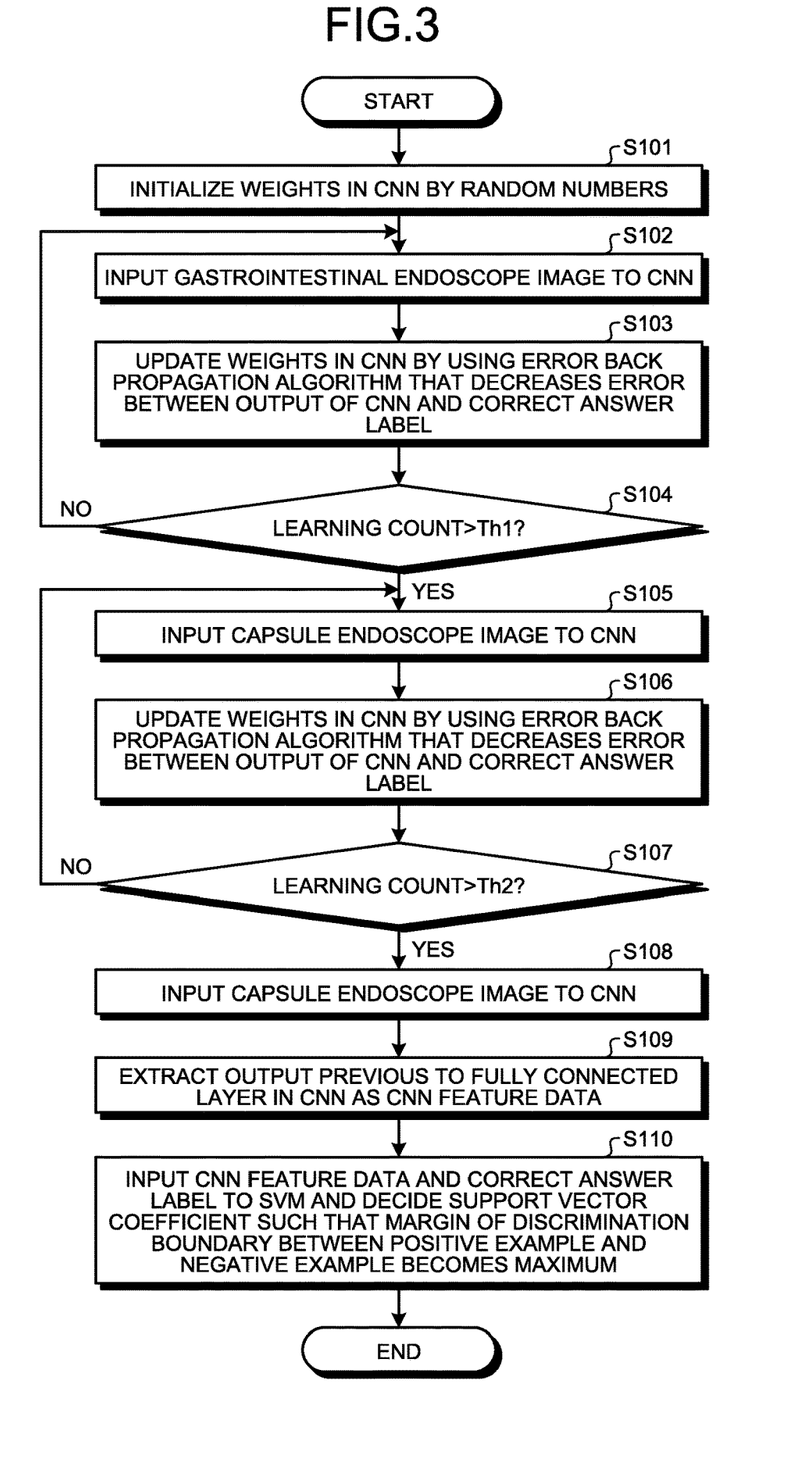
FIG. 3 is a flowchart illustrating the outline of a learning process performed by the image recognition device according to the first embodiment of the present disclosure.

In the following, the learning process performed by the image recognition device 4 will be described. FIG. 3 is a flowchart illustrating the outline of the learning process performed by the image recognition device 4.

As illustrated in FIG. 3, first, the control unit 45 initializes the weights in the CNN 50 by random numbers (Step S101).

Then, the control unit 45 causes the CNN 50 to input a gastrointestinal endoscope image from the gastrointestinal endoscope image database 2 via the acquiring unit 41 (Step S102).

Then, the control unit 45 updates the weights in the CNN 50 by using the error back propagation that decreases an error between the output of the CNN 50 and the correct answer label (+1, −1, etc.) that is received from the gastrointestinal endoscope image database 2 (Step S103). Specifically, as illustrated in FIG. 2, the CNN 50 performs, on the gastrointestinal endoscope image, a convolution process at the convolution layer 501 and a pooling process at the pooling layer 502 alternately three times, according to forward propagation, and performs, on the gastrointestinal endoscope image, a fully connection process at the fully connected layer 503 twice, according to forward propagation. Then, the error calculating unit 51 calculates the first error between the first correct answer label and the output from the fully connected layer 503. Subsequently, the control unit 45 performs the pre-training (the first learning) that updates the weights of the parameters in the CNN 50, according to back propagation of the first error calculated by the error calculating unit 51 in the order of the fully connected layer 503, the pooling layer 502, and the convolution layer 501.

Thereafter, if the number of images learned in the pre-training by the CNN 50 exceeds a predetermined threshold Th1 (Yes at Step S104), the process in the image recognition device 4 proceeds to Step S105. In contrast, if the number of images learned in the pre-training by the CNN 50 does not exceed the predetermined threshold Th1 (No at Step S104), the process in the image recognition device 4 returns to Step S102 described above.

At Step S105, the control unit 45 causes the CNN 50 to input a capsule endoscope image from the capsule endoscope image database 3 via the acquiring unit 41.

Then, the control unit 45 updates the weights in the CNN 50 by using the error back propagation that decreases an error between an output of the CNN 50 and the correct answer label (+1, −1, etc.) that is received from the capsule endoscope image database 3 (Step S106).

Specifically, as illustrated in FIG. 2, the CNN 50 performs, on the capsule endoscope image, the convolution processes at the convolution layer 501 and the pooling processes at the pooling layer 502 alternately tree times, according to the forward propagation, and performs, on the capsule endoscope image, the fully connection process at the fully connected layer 503 twice, according to the forward propagation. Then, the error calculating unit 51 calculates the second error between the second correct answer label and the output form the fully connected layer 503. Subsequently, the control unit 45 performs fine-tuning (the second learning) that updates weights in the CNN 50, according to the back propagation of the second error calculated by the error calculating unit 51 in the order of the fully connected layer 503, the pooling layer 502, and the convolution layer 501.

Then, if the number of images learned in the fine-tuning by the CNN 50 exceeds a predetermined threshold Th2 (Yes at Step S107), the process in the image recognition device 4 proceeds to Step S108. In contrast, if the number of images learned in the fine-tuning by the CNN 50 does not exceed the predetermined threshold Th2 (No at Step S107), the image recognition device 4 returns to Step S105 described above.

At Step S108, the control unit 45 causes the CNN 50 to input a capsule endoscope image from the capsule endoscope image database 3 via the acquiring unit 41.

Subsequently, the CNN 50 extracts an intermediate output that is previous to the fully connected layer 503 as CNN feature data of the second image group (Step S109). Specifically, the CNN 50 performs, on the capsule endoscope image that has been input via the acquiring unit 41, the convolution process at the convolution layer 501 and the pooling process at the pooling layer 502 alternately three times, according to the forward propagation, and then the CNN 50 extracts the obtained results as the CNN feature data of the second image group.

Then, based on the CNN feature data that has been input from the CNN 50 and based on the second correct answer label that has been input from the capsule endoscope image database 3, the SVM 52 determines a support vector coefficient such that a margin of a discrimination boundary between the positive example and the negative example becomes the maximum (Step S110). After the process at Step S110, the image recognition device 4 ends the process.

In this way, in the image recognition device 4, first, the CNN 50 uses both the gastrointestinal endoscope image groups and the first correct answer labels and performs the pre-training (the first learning) that updates the weights in the parameters according to the error back propagation that decreases an error between the gastrointestinal endoscope image group and the first correct answer label. Next, the CNN 50 uses the capsule endoscope image group and the second correct answer label and then performs the fine-tuning (the second learning) that updates the parameters according to the error back propagation that reduces the error between the capsule endoscope image group and the second correct answer label. Then, the CNN 50 extracts the intermediate output of the CNN 50 as the CNN feature data of the capsule endoscope image group. Subsequently, by using the CNN feature data extracted by the CNN 50 and by using the second correct answer label, the SVM 52 learns for classification of an input image with respect to the capsule endoscope image group or learns for detection of the recognition target object (third learning). Then, the SVM 52 classifies unknown capsule endoscope image groups that are input from the acquiring unit 41 or detects the recognition target object. Consequently, it is possible to perform image recognition with high accuracy on the recognition target having insufficient learning purpose images.

Recognition Process

Figure 4:
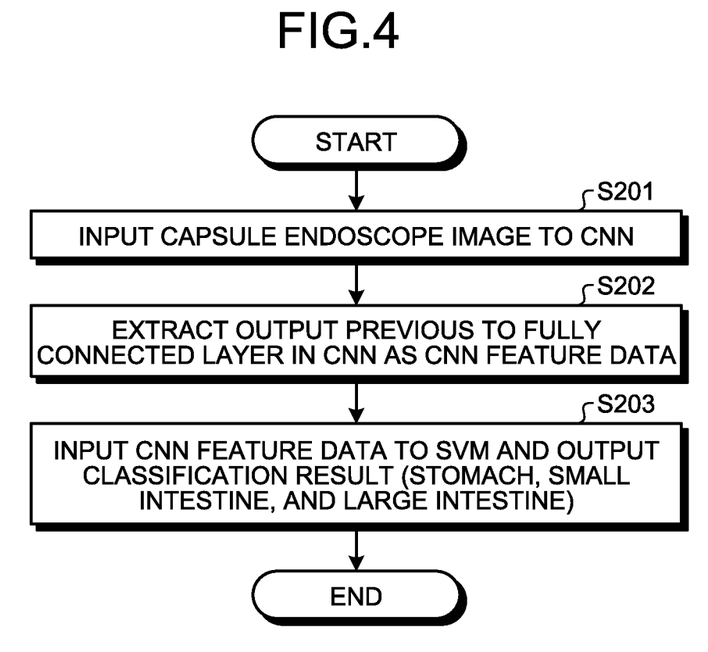
FIG. 4 is a flowchart illustrating the outline of a recognition process performed by the image recognition device according to the first embodiment of the present disclosure.

In the following, a description will be given of the recognition process in which the image recognition device 4 recognizes unknown image by using the learned CNN 50 and the learned SVM 52. FIG. 4 is a flowchart illustrating, in outline, the recognition process performed by the image recognition device 4. Furthermore, in the following, a description will be given of an example in which a capsule endoscope image captured by a capsule endoscope device is used as an unknown image.

As illustrated in FIG. 4, first, the control unit 45 causes the CNN 50 to input an unknown capsule endoscope image from outside via the acquiring unit 41 (Step S201).

Then, the CNN 50 extracts, as the CNN feature data, an output that is previous to the fully connected layer 503 (Step S202). Specifically, the CNN 50 performs, on the capsule endoscope image that has been input via the acquiring unit 41, the convolution process at the convolution layer 501 and the pooling process at the pooling layer 502 alternately three times, according to the forward propagation and then the CNN 50 extracts the results as the CNN feature data.

Then, the SVM 52 inputs the CNN feature data from the CNN 50 and outputs the classification result (one of the stomach, the small intestine, and the large intestine, for example) (Step S203). For example, the SVM 52 outputs information indicating that the stomach is in the unknown capsule endoscope image. After the process at Step S203, the image recognition device 4 ends the process.

In this way, by using the learned CNN 50 and the learned SVM 52, the image recognition device 4 can recognize the unknown capsule endoscope image and perform classification.

Landmark Process

In the following, a description will be given of a landmark process in which the image recognition device 4 estimates a changing position of organs performed on an organ classification result sequence of temporal continuous time series images. In the following, as a method of classifying images into two categories, an example in which images of the stomach and the small intestine are automatically classified (discriminated) will be described. The learned SVM 52 determines (classifies) whether the target object of the temporal continuous capsule endoscope images is the stomach or the small intestine. Then, the organ changing position determination unit 53 extracts (determines) a candidate for a changing position of the stomach and the small intestine based on a degree of similarity between this determination result and a step function. Then, as will be described later, the organ changing position determination unit 53 determines a correct answer position of the organs to be distinguished, such as the pylorus or the ileocecal valve. Here, the temporal continuous capsule endoscope images are unclassified (unknown labeled) images arranged in chronological order of the captured images and are, specifically, moving images captured at a predetermined frame rate (for example, 60 fps or 30 fps) or images obtained by interval imaging at a predetermined interval (for example, 2 fps or 4 fps).

Figure 5:
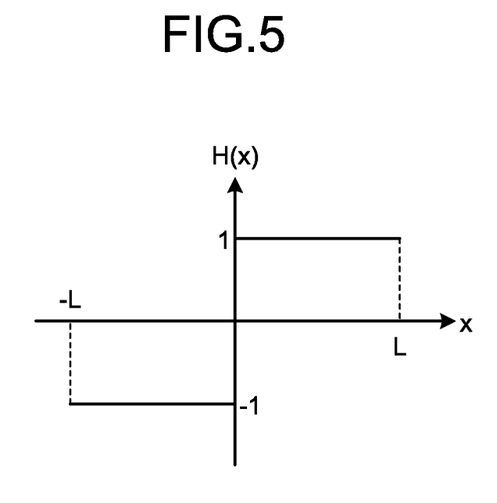
FIG. 5 is a diagram schematically illustrating an example of a step function used in a landmark process performed by the image recognition device according to the first embodiment of the present disclosure.
Figure 6:
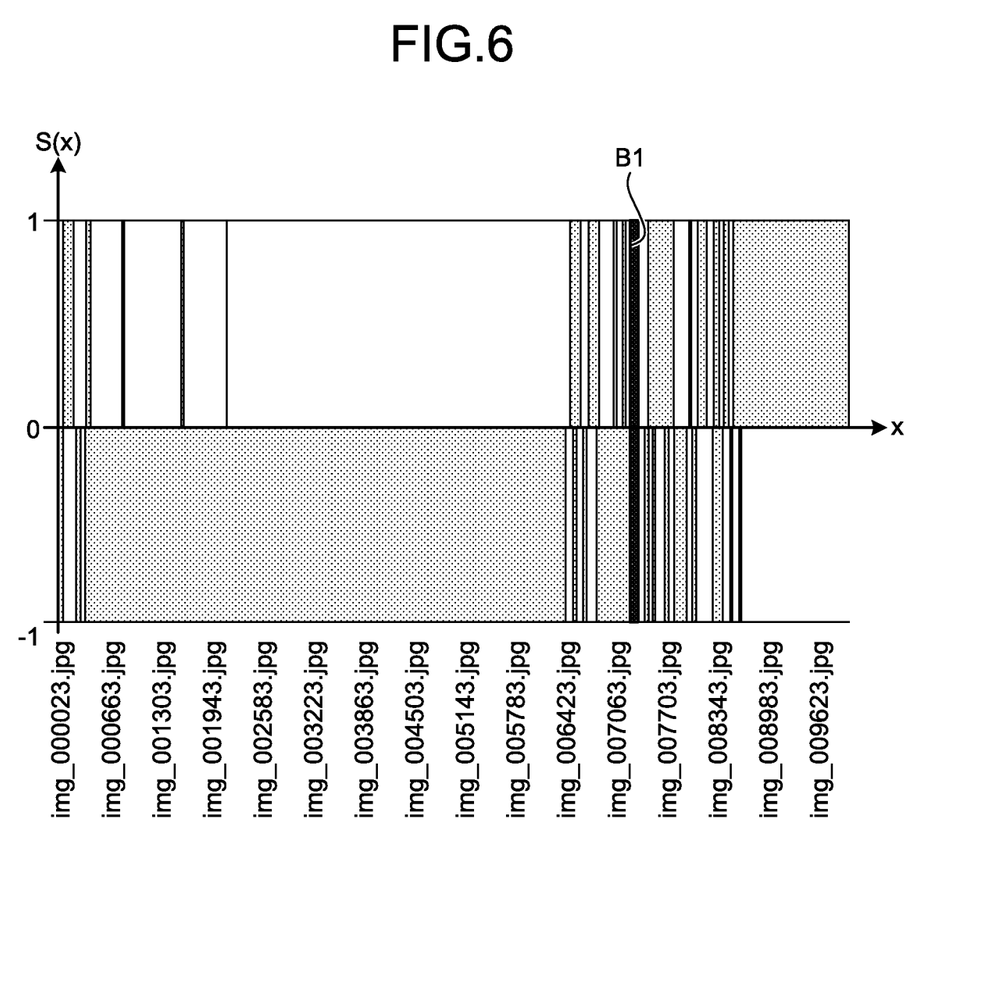
FIG. 6 is a diagram illustrating an example of automatically classifying time series image groups of the stomach and the small intestine in the landmark process performed by the image recognition device according to the first embodiment of the present disclosure.

FIG. 5 is a diagram schematically illustrating an example of the step function used in the landmark process performed by the image recognition device 4. FIG. 6 is a diagram illustrating an example of automatically classifying (determination result) time series image groups of the stomach and the small intestine. In FIG. 6, the vertical axis represents the determination results of the SVM 52 and the horizontal axis represents the time series image numbers. Furthermore, in FIG. 6, the determination result $S(x)=-1$ of the SVM 52 represents the stomach and $S(x)=+1$ represents the small intestine. In the image, numbers indicated by img000023 to img009623 are attached in chronological order, and determination results (classification results) $S(x)$ are arrayed in chronological order. Furthermore, in FIG. 6, a line B1 represents the pylorus that is the correct answer position of a changing from the stomach to the small intestine. Furthermore, in FIG. 6, it is assumed that the image numbers are sampled at a predetermined interval.

The organ changing position determination unit 53 obtains an evaluation value $Conv(x)$ indicated in Equation (1) below by performing the convolution process (convolution operation process) of a step function $H(x)$ illustrated in FIG. 5 and the determination results $S(x)$ illustrated in FIG. 6. Then, the organ changing position determination unit 53 extracts the organ changing position based on the evaluation value $Conv(x)$ and Equation (2).

$$\underset{L}{Conv}(x) = \frac{1}{2L}\sum_{y=-L}^{y=L} S(x-y)H(y) \quad (1)$$

$$\text{Organ changing position} = \underset{x}{Arg}\left[\sum_{L=L0}^{L=L1} \underset{L}{Conv}(x)\right] \quad (2)$$

Here, the step function $H(x)$ illustrated in FIG. 5 is a function defined in a region of $x=-L$ to $+L$ and the window width L thereof is variable. Furthermore, the organ changing position determination unit 53 arbitrarily fixes the window width L in Equation (1) above and calculates the evaluation value $Conv(x)$ based on the convolution process after normalizing the value obtained by dividing by $2L$.

Furthermore, in the square brackets of Equation (2) above, the organ changing position determination unit 53 arbitrarily fixes a position x and calculates the minimum value of $Conv(x)$ within the range of the window width L between L0 (for example, 10) and L1. Here, if a search start position of an image is set to M0 and a search end position of the image is set to M1, $L1=MIN[x-M0, M1-x]$ is obtained. For example, it is assumed that $M0=1$ and $M1=10000$.

Then, the organ changing position determination unit 53 extracts, based on an Arg function, the position x with the minimum value as a changing position of an organ. Furthermore, while the organ changing position determination unit 53 uses the minimum value of $Conv(x)$ in Equation (2) described above in this embodiment, the maximum value of $Conv(x)$ may also be used in other embodiments.

Figure 7:
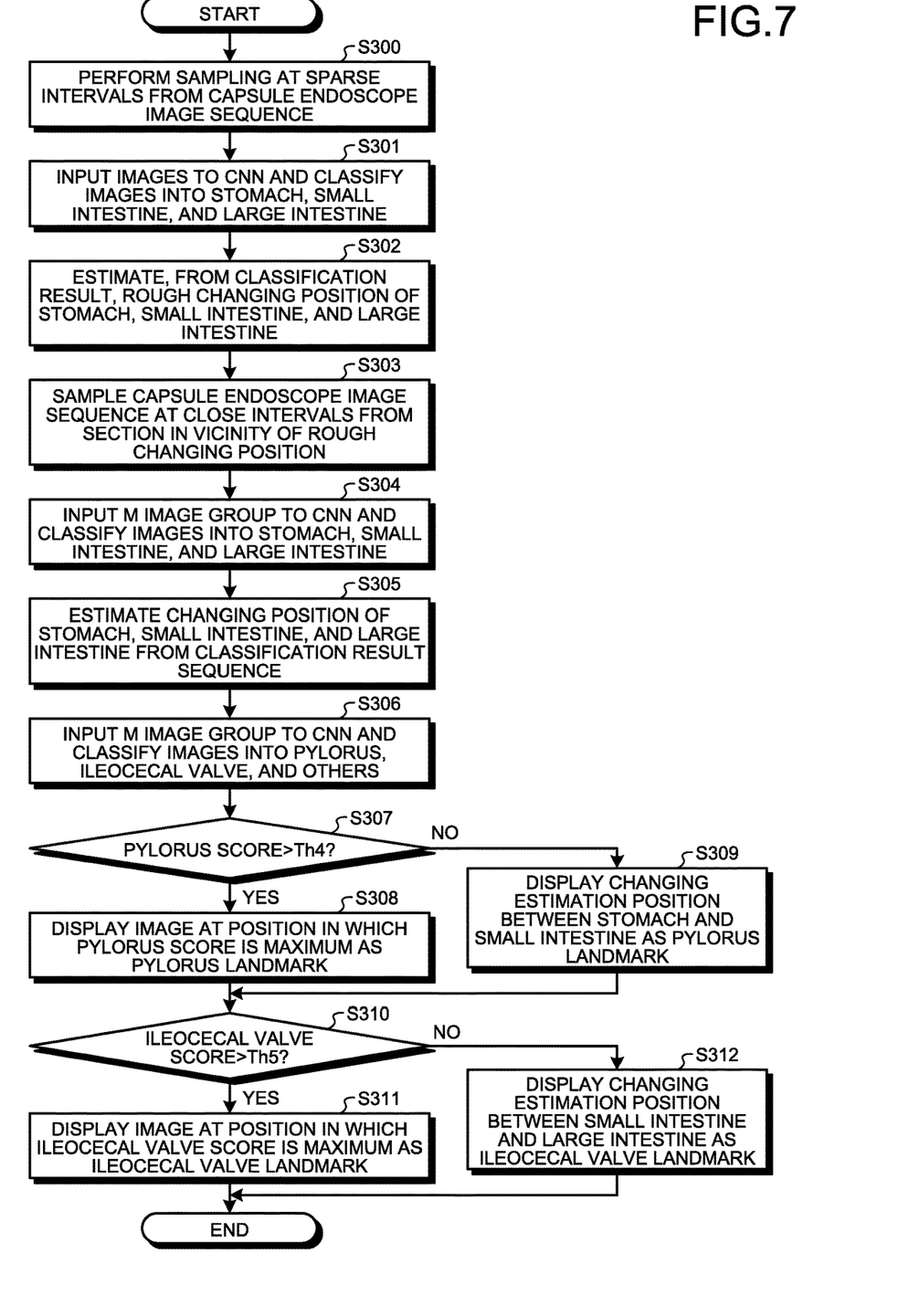
FIG. 7 is a flowchart illustrating the outline of the landmark process performed by the image recognition device according to the first embodiment of the present disclosure.

In the following, the landmark process performed by the image recognition device 4 will be described in detail. FIG. 7 is a flowchart illustrating the outline of the landmark process performed by the image recognition device 4.

As illustrated in FIG. 7, first, the acquiring unit 41 performs sampling at relatively sparse intervals (for example, 50 images interval) from the capsule endoscope image sequence that is input from outside (Step S300).

Then, the control unit 45 causes the learned CNN 50 to input each of the images sampled at sparse intervals from the capsule endoscope image sequence by the acquiring unit 41, and allows the learned CNN 50 to classify the images into the categories of the stomach, the small intestine, and the large intestine (Step S301).

Subsequently, at Step S301 described above, the organ changing position determination unit 53 estimates, from the classification result sequence obtained by the CNN 50, a rough changing position between the stomach and the small intestine and between the small intestine and the large intestine by using the calculation method described above (Step S302).

Then, the acquiring unit 41 samples the capsule endoscope image sequence that has been input from outside at relatively dense intervals from the section in the vicinity of the rough changing position estimated by the organ changing position determination unit 53 at Step S302 (for example, all 200 images before and after a rough estimated position) (Step S303). Here, the image group of the capsule endoscope sampled at dense intervals from the section in the vicinity of the rough changing position is referred to as an M image group.

Subsequently, the control unit 45 causes the learned CNN 50 to input the sampled M image group by the acquiring unit 41, and allows the learned CNN 50 to classify the images into the categories of the stomach, the small intestine, and the large intestine (Step S304).

Then, based on the classification result obtained by the CNN 50 at Step S304, the organ changing position determination unit 53 more accurately estimates changing positions between the stomach and the small intestine and between the small intestine and the large intestine by using the method described above (Step S305).

Subsequently, regarding the M image group, after having performed pre-training on three categories, i.e., the pylorus representing the exact changing position between the stomach and the small intestine, the ileocecal valve representing the exact changing position between the small intestine and the large intestine, and others except for the above two positions by using the gastrointestinal endoscope images, the control unit 45 outputs the obtained result to the CNN 50 that has performed fine-tuning by using the capsule endoscope images, whereby the control unit 45 allows the CNN 50 to classify the images into the categories of the pylorus, the ileocecal valve, and the others (Step S306). In this case, the CNN 50 calculates the pylorus score corresponding to the reliability of the pylorus and the ileocecal valve score corresponding to the reliability of the ileocecal valve.

Then, if the pylorus score calculated by the CNN 50 is greater than a predetermined threshold Th4 (Yes at Step S307), the control unit 45 allows the display 43 to display the image at the position having the maximum pylorus score as a pylorus landmark (Step S308). After Step S308, the process in the image recognition device 4 proceeds to Step S310 that will be described later.

At Step S307, if the pylorus score calculated by the CNN 50 is the predetermined threshold Th4 or less (No at Step S307), because the pylorus is not possibly imaged in the M image group, the control unit 45 allows the display unit 43 to display the image at a changing estimation position between the stomach and the small intestine estimated at Step S305 as the pylorus landmark (Step S309). After Step S309, the process in the image recognition device 4 proceeds to Step S310 that will be described later.

Subsequently, if the ileocecal valve score calculated by the CNN 50 is greater than a predetermined threshold Th5 (Yes at Step S310), the control unit 45 allows the display unit 43 to display the image at the position having the maximum ileocecal valve score as the ileocecal valve landmark (Step S311). After Step S311, the image recognition device 4 ends the process.

At Step S310, if the ileocecal valve score is the predetermined threshold Th5 or less (No at Step S310), because the ileocecal valve is not possibly be imaged in the M image group, the control unit 45 allows the display unit 43 to display the changing estimation position between the small intestine and the large intestine estimated at Step S305 as the ileocecal valve landmark (Step S312). After Step S312, the image recognition device 4 ends the process.

According to the first embodiment described above, after the CNN 50 performs, by using the gastrointestinal endoscope image group and the first correct answer label, the pre-training that updates the weights of the parameters by using the error back propagation that decreases an error between the gastrointestinal endoscope image group and the first correct answer label, the CNN 50 performs, by using the capsule endoscope image group and the second correct answer label, the fine-tuning that updates the parameters by using the error back propagation that decreases an error between the capsule endoscope image group and the second correct answer label and then extracts an intermediate output of the CNN 50 as the feature data of the capsule endoscope image group. Then, the SVM 52 performs, by using the feature data of the capsule endoscope image group extracted by the CNN 50 and the second correct answer label, the third learning that learns for classification of the input image or detection of the recognition target object. Consequently, it is possible to implement image recognition with high accuracy on the recognition target having insufficient learning purpose images.

Furthermore, according to the first embodiment, instead of the capsule endoscope image group captured through liquid (for example, water, digestive fluid, etc.) by the capsule endoscope that is forwarded by peristaltic movement of an alimentary canal, by indirectly using, as a pre-training purpose image, a gastrointestinal endoscope image group that has been captured through air by a gastrointestinal endoscope in which an imaging direction is adjusted by a doctor, thereby providing a different appearance from that by the capsule endoscope, it is possible to perform more accurate learning when compared with a case in which a video image obtained by a digital camera or another medical device is used for the pre-training.

First Modification of the First Embodiment

In the following, a first modification of the first embodiment according to the present disclosure will be described. The first modification of the first embodiment has the same configuration as that described above in the first embodiment and has a different learning process performed by the image recognition device. In a description below, the learning process performed by an image recognition device according to the first modification of the first embodiment will be described. Furthermore, the same reference numerals are assigned to components that are identical to those in the image recognition device 4 according to the first embodiment, and repetitive descriptions thereof will be omitted.

Learning Process

Figure 8:
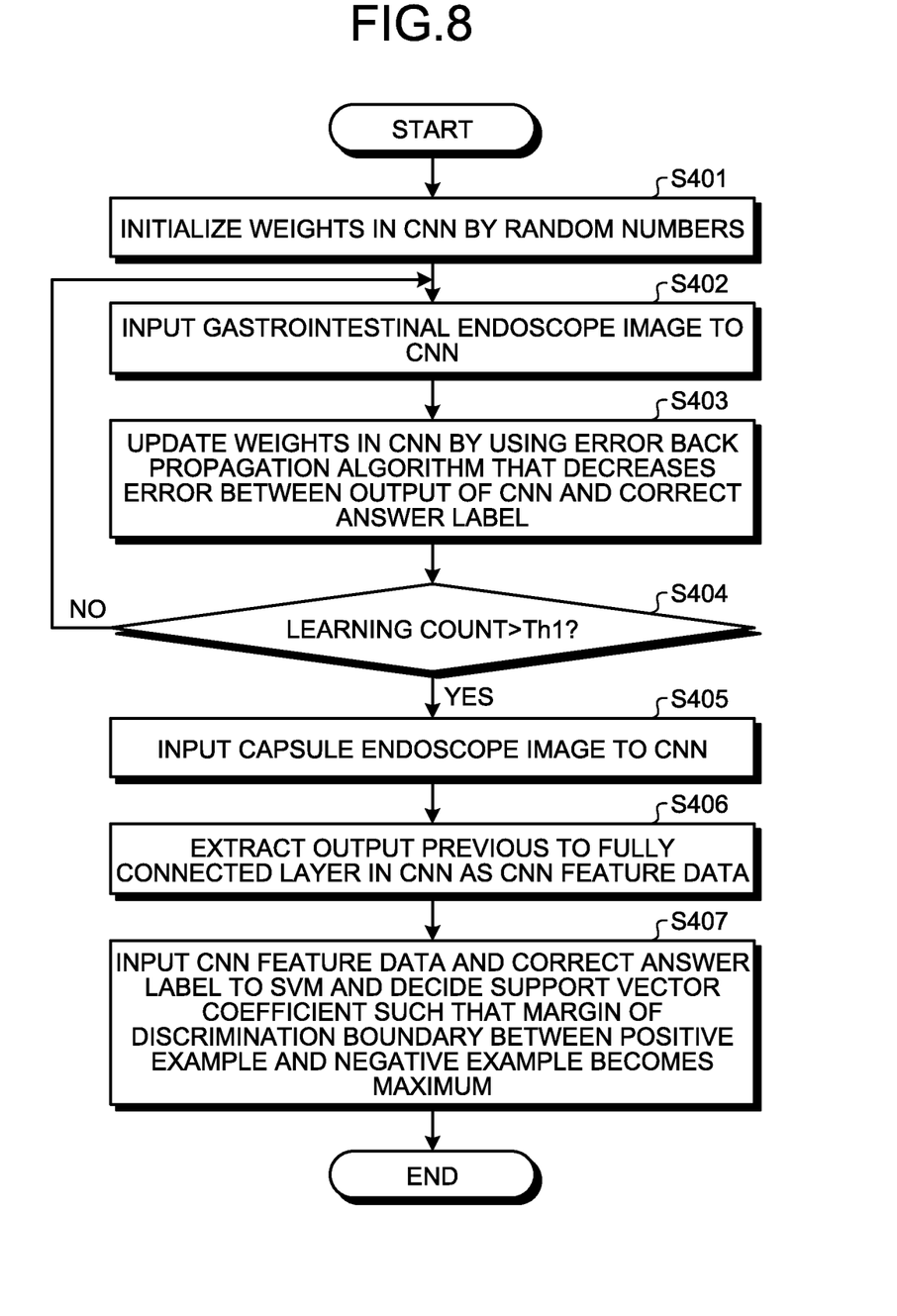
FIG. 8 is a flowchart illustrating the outline of a learning process performed by an image recognition device according to a first modification of the first embodiment of the present disclosure.

FIG. 8 is a flowchart illustrating the outline of a learning process performed by the image recognition device 4 according to the first modification of the first embodiment. In FIG. 8, Steps S401 to S404 correspond to Steps S101 to S104, respectively, described above with reference to FIG. 3 and correspond to the pre-training (the first learning) performed by the CNN 50 by using the gastrointestinal endoscope image group. Furthermore, Steps S405 to S407 correspond to Steps S108 to S110, respectively, described above with reference to FIG. 3 and correspond to the learning process (the second learning) performed by the SVM 52 by using the capsule endoscope image group. After Step S407, the image recognition device 4 ends the process.

According to the first modification of the first embodiment described above, by omitting the fine-tuning performed by the CNN 50 by using the capsule endoscope image, the learning time needed for the CNN 50 can be reduced.

Second Modification of the First Embodiment

In the following, a second modification of the first embodiment according to the present disclosure will be described. The second modification according to the first embodiment has the same configuration as that described in the first embodiment and has a different learning process performed by the image recognition device. In a description below, a learning process performed by the image recognition device according to the second modification of the first embodiment will be described. Furthermore, the same reference numerals are assigned to components that are identical to those in the image recognition device 4 according to the first embodiment, and repetitive descriptions thereof will be omitted.

Learning Process

Figure 9:
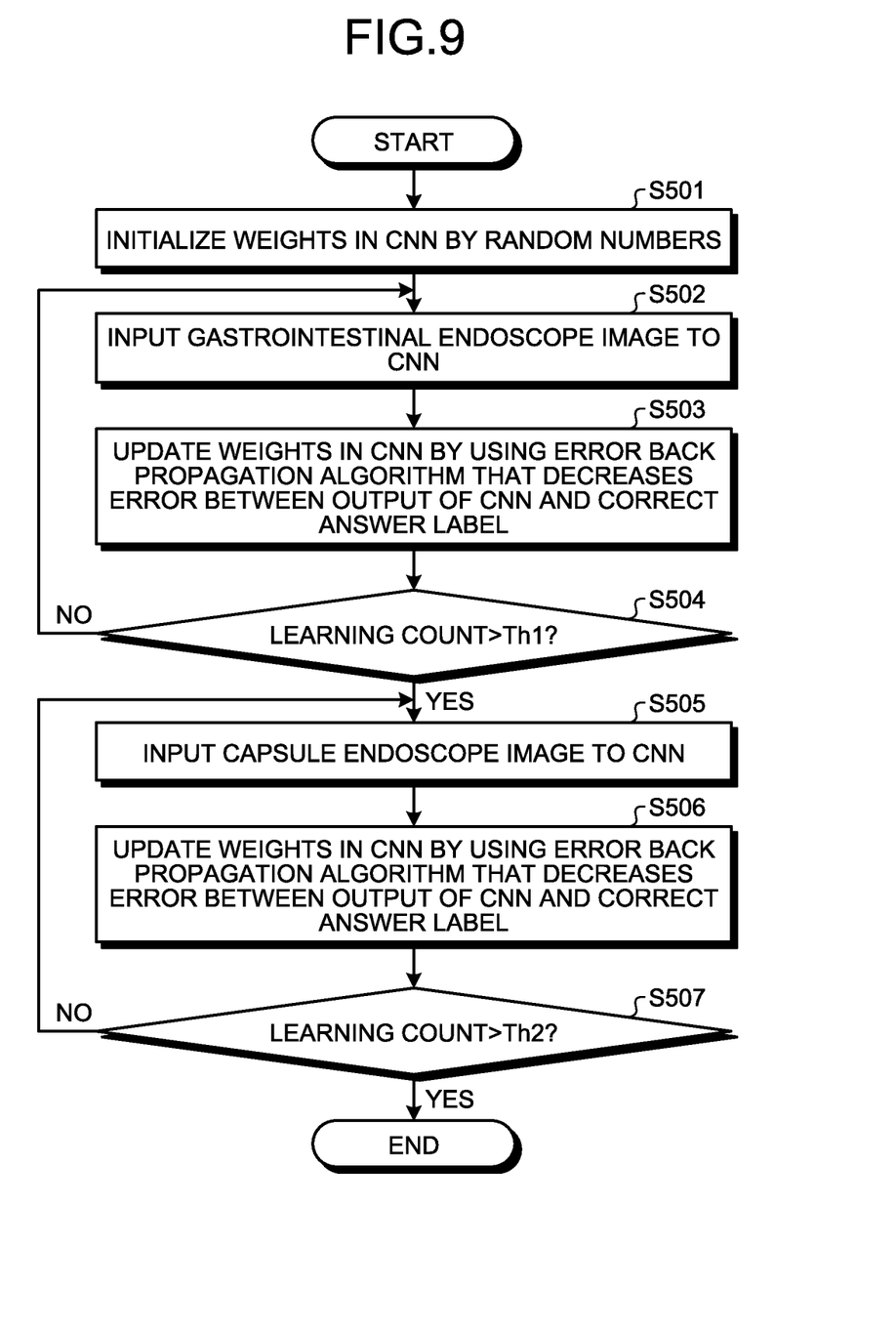
FIG. 9 is a flowchart illustrating the outline of a learning process performed by an image recognition device according to a second modification of the first embodiment of the present disclosure.

FIG. 9 is a flowchart illustrating the outline of a learning process performed by the image recognition device 4 according to the second modification of the first embodiment. In FIG. 9, Steps S501 to S504 correspond to Steps S101 to S104, respectively, described above with reference to FIG. 3 and correspond to the pre-training (the first learning) performed by the CNN 50 by using the gastrointestinal endoscope image. Furthermore, Steps S505 to S507 correspond to Steps S105 to S107 respectively, described above with reference to FIG. 3 and correspond to the fine-tuning (the second learning) performed by the CNN 50 by using the capsule endoscope image.

According to the second modification of the first embodiment described above, it is possible to omit the learning performed by the SVM 52 by using the capsule endoscope image.

Second Embodiment

In the following, a second embodiment of the present disclosure will be described. The second embodiment has the same configuration as that described above in the first embodiment and has a different learning process performed by the image recognition device. Specifically, in the first embodiment, a description has been given of image classification performed on a capsule endoscope image group; however, in the second embodiment, learning is also performed on information related to a rough position and the size of a lesion or the like. Furthermore, the same reference numerals are assigned to components that are identical to those described above in the first embodiment, and repetitive descriptions thereof will be omitted.

Learning Process

Figure 10:
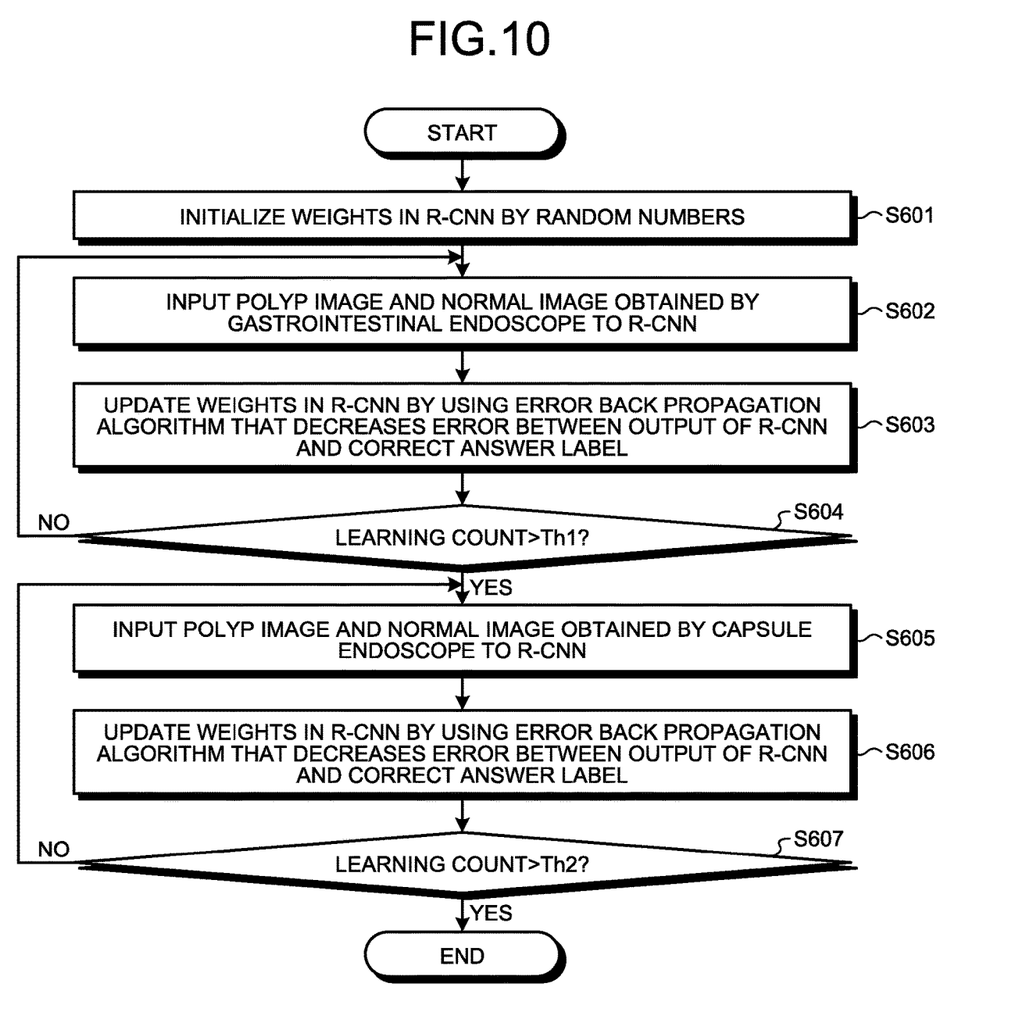
FIG. 10 is a flowchart illustrating the outline of a learning process performed by an image recognition device according to a second embodiment of the present disclosure.

FIG. 10 is a flowchart illustrating the outline of a learning process performed by the image recognition device 4 according to the second embodiment. Furthermore, in FIG. 10, a description will be given, as an example, with the assumption that a type of the CNN 50 is Faster R-CNN (hereinafter, referred to as an "R-CNN 50"). Furthermore, in FIG. 10, a description will be given of a case in which, instead of the fully connected layer 503 described in the first embodiment, the R-CNN 50 is set as a network that learns the position and the size (four vertices of a rectangle) of a rectangular area (Bounding Box) in which an object is present and that performs regression and classification. Furthermore, in FIG. 10, in an output of the last layer of the convolution layer and the pooling layer in the R-CNN 50, rather than in an image, Fully-CNN is used instead of sliding the rectangular area.

In FIG. 10, first, the control unit 45 initializes the weights in the R-CNN 50 by random numbers (Step S601).

Subsequently, the control unit 45 causes the R-CNN 50 to input a polyp image and a normal image obtained by the gastrointestinal endoscope from the gastrointestinal endoscope image database 2 via the acquiring unit 41 (Step S602).

Then, the control unit 45 updates the weights in the R-CNN 50 based on the error back propagation that decreases an error between an output of the R-CNN 50 and the correct answer label (+1, −1, etc.) received from the gastrointestinal endoscope image database 2 (Step S603). Consequently, the R-CNN 50 can perform pre-training (the first learning) on the polyp image and the normal image obtained by the gastrointestinal endoscope.

Subsequently, if the number of images learned in the pre-training performed by the R-CNN 50 exceeds the predetermined threshold Th1 (Yes at Step S604), the process in the image recognition device 4 proceeds to Step S605. In contrast, if the number of images in the pre-training performed by the R-CNN 50 does not exceed the predetermined threshold Th1 (No at Step S604), the image recognition device 4 returns to Step S602 described above.

At Step S605, the control unit 45 causes the R-CNN 50 to input a polyp image and a normal image obtained by the capsule endoscope via the acquiring unit 41.

Subsequently, the control unit 45 updates the weights in the R-CNN 50 by using the error back propagation that decreases an error between an output of the R-CNN 50 and the correct answer label (+1, −1, etc.) obtained from the capsule endoscope image database 3 (Step S606).

Consequently, by performing the fine-tuning (the second learning) on the polyp image and the normal image obtained from the capsule endoscope, the R-CNN 50 can form a network that is used for regression and classification and in which the position (coordinates) and the size of a lesion can be recognized.

Then, if the number of images learned in the fine-tuning performed by the R-CNN 50 exceeds the predetermined threshold Th2 (Yes at Step S607), the image recognition device 4 ends the process. In contrast, if the number of images learned in the fine-tuning performed by the R-CNN 50 does not exceed the predetermined threshold Th2 (No at Step S607), the process in the image recognition device 4 returns to Step S605 described above.

According to the second embodiment described above, it is possible to implement image recognition with high accuracy on the recognition target having the insufficient number of images of learning purpose.

Furthermore, according to the second embodiment, if a capsule endoscope image sequence is input to the R-CNN 50, it is possible to output a rectangular area of a polyp candidate.

Furthermore, in the second embodiment, a Faster R-CNN is used for the R-CNN 50; however, OverFeat, a spatial pyramid pooling network (SPP_Net) or a CNN other than these may also be used.

Other Embodiments

As a CNN according to the present disclosure, a known network may also be used. For example, a CNN may also be formed by using VGG-16. In this case, VGG-16 uses a convolution filter with the size of 3×3 and applies a convolution result of the input image to a nonlinear function ReLU. Then, after two layers or three layers of convolution layers are sequentially gone through in VGG-16, Max Pooling (sub sampling that selects the maximum value included in the output with the size of 2×2 in a previous layer) is used. Incidentally, in VGG-16, the number of the pooling layers is not included in the total number of layers. Namely, VGG-16 is formed of 13 convolution layers, five Max Pooling layers, and three fully connected layers. Even when VGG-16 is used as a CNN, by performing the fine-tuning (the second learning) by using the capsule endoscope image after having performed the pre-training learning (the first learning) by using the gastrointestinal endoscope image, it is possible to obtain the same configuration as that used in the above described embodiment. Furthermore, VGG-16 has been described as a configuration example of the CNN; however, for example, it is possible to form by using one of Alex-net, Z_F-net that is an improved version of Alex-net, GoogLeNet, and Network in Network or, alternatively, it is possible to form by appropriately combining these networks.

Furthermore, in the present disclosure, the above-described processes are implemented by executing the image processing program recorded in a recording device in a computer system, such as a personal computer or a workstation. Furthermore, this type of computer system may also be used by connecting to another computer system or a device, such as a server, via a local area network (LAN), a wide area network (WAN), or a public circuit, such as the Internet. In this case, the image recognition device according to the first and the second embodiments and the modifications thereof may also acquire image data of an intraluminal image via these networks, may also output image processing results to various output devices, such as viewers or printers, that are connected via these networks, or may also store the image processing results in a storage device such as a recording medium or the like that can be read by a reading device connected to, for example, a network, connected via these networks.

According to the present disclosure, an advantage is provided in that it is possible to implement image recognition with high accuracy on a recognition target having insufficient learning purpose images.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A learning method performed by an image recognition device that includes a convolutional neural network, the learning method comprising:
   performing first learning by the convolutional neural network by using a first image group captured by a first type of endoscope at a first frame rate, the first image group being input from a source external to the image recognition device; and
   performing, after performing the first learning, second learning by using a second image group that is captured by a second type of endoscope different from the first type of endoscope at a second frame rate that is lower than the first frame rate, the second image group being input from a source external to the image recognition device, and a number of images in the second image group being less than a number of images in the first image group.

2. The learning method according to claim 1, wherein:
   the first learning is pre-training that updates weights in the convolutional neural network in accordance with an error back propagation that decreases an error between an output of the convolutional neural network and a correct answer label attached to the first image group, and
   the second learning is fine-tuning that updates the weights by using the convolutional neural network in which the weights have been updated by the pre-training.

3. The learning method according to claim 2, further comprising performing third learning that extracts an intermediate output of the convolutional neural network in which the weights have been updated by the fine-tuning as feature data of the second image group and that learns for classification of an input image or detection of a recognition target object by a learning machine by using a correct answer label attached to the second image group and by using the feature data.

4. The learning method according to claim 3, further comprising performing, after performing the third learning, classification of the input image or detection of the recognition target object by the learning machine by using the second image group.

5. The learning method according to claim 1, wherein:
   the first learning is pre-training that updates the weights in the convolutional neural network by an error back propagation algorithm that decreases an error between an output of the convolutional neural network and a correct answer label included in the first image group, and
   the second learning extracts feature data of the second image group by using the convolutional neural network in which the weights in the convolutional neural network have been updated by the pre-training and learns for classification of an input image or detection of a recognition target object by a learning machine by using the correct answer label of the second image group and the feature data.

6. The learning method according to claim 5, further comprising performing, after performing the second learning, classification of the input image or detection of the recognition target object by the learning machine by using the second image group.

7. The learning method according to claim 1, wherein the second image group is an image group obtained from interval shooting.

8. The learning method according to claim 1, wherein:
   the first type of endoscope is an endoscope that can be inserted in a subject, and
   the second type of endoscope is a capsule endoscope that is swallowed by a subject and is discharged outside the subject after a predetermined time.

9. The learning method according to claim 1, wherein:
   the first type of endoscope is an endoscope that can be inserted in a subject, and
   the second type of endoscope is a battery-powered endoscope.

10. An image recognition device that includes a convolutional neural network, the image recognition device comprising:
    a processor comprising hardware, the processor being configured to:
      acquire each of a first image group captured at a first frame rate and a second image group that is captured at a second frame rate that is lower than the first frame rate, a number of images in the second image group being less than a number of images in the first image group;
      calculate, after the first image group is input to the convolutional neural network, a first error between an output result of the convolutional neural network and a correct answer label attached to the first image group; and
      update the weights in the convolutional neural network by back propagation performed on the first error through the convolutional neural network,
    wherein the processor is further configured to:
      calculate, after the weights have been updated and then the second image group is input to the convolutional neural network, a second error between the output result of the convolutional neural network and the correct answer label attached to the second image group; and
      update the weights in the convolutional neural network by back propagation performed on the second error through the convolutional neural network.

11. The image recognition device according to claim 10, wherein the processor is further configured to learn, after the weights have been updated, by using an intermediate output of the convolutional neural network extracted as feature data of the second image group by the convolutional neural network and by using the correct answer label of the second image group, for classification of an input image or detection of a recognition target object.

12. The image recognition device according to claim 11, wherein the processor is further configured to perform, after having learned the second image group, one of classification of the input image and detection of the recognition target object by using the second image group.

13. The image recognition device according to claim 12, wherein the processor is further configured to implement a support vector machine, and the one of the classification and the detection is performed by the support vector machine.

14. An image recognition device that includes a convolutional neural network, the image recognition device comprising:

a processor comprising hardware, the processor being configured to:
- acquire each of a first image group captured at a first frame rate and a second image group that is captured at a second frame rate that is lower than the first frame rate, a number of images in the second image group being less than a number of images in the first image group;
- calculate, after the first image group is input to the convolutional neural network, a first error between an output result of the convolutional neural network and a correct answer label attached to the first image group;
- update the weights in the convolutional neural network by back propagation performed on the first error through the convolutional neural network; and
- learn for classification of an input image or detection of a recognition target object in an image by using the second image group, wherein the processor is further configured to learn, after the weights have been updated, by using an intermediate output of the convolutional neural network extracted as feature data of the second image group by the convolutional neural network and by using the correct answer label of the second image group, for classification of the input image or detection of the recognition target object in the image.

15. The image recognition device according to claim 14, wherein the processor is further configured to implement a support vector machine, and one of the classification and the detection is performed by the support vector machine.

16. An image recognition apparatus comprising a processor that performs processing based on a convolutional neural network, wherein the convolutional neural network has been learned by performing:
- first learning by the convolutional neural network, by using a first image group captured by a first type of endoscope at a first frame rate, the first image group being input from a source external to the image recognition apparatus; and
- second learning, after performing the first learning, by using a second image group that is captured by a second type of endoscope different from the first type of endoscope at a second frame rate that is lower than the first frame rate, the second image group being input from a source external to the image recognition apparatus, and a number of images in the second image group being less than a number of images in the first image group.

* * * * *